United States Patent [19]

Benedict

[11] 4,399,817
[45] Aug. 23, 1983

[54] BORON CONTAINING POLYPHOSPHONATES FOR THE TREATMENT OF CALCIFIC TUMORS

[75] Inventor: James J. Benedict, Cincinnati, Ohio

[73] Assignee: The Procter & Gamble Company, Cincinnati, Ohio

[21] Appl. No.: 278,969

[22] Filed: Jun. 30, 1981

[51] Int. Cl.³ .................. A61K 49/00; A61N 5/06
[52] U.S. Cl. .............................. 406/20; 128/783; 260/502.4 P; 424/1
[58] Field of Search ............ 128/207.21, 783, 804, 128/399; 260/502.4 P; 424/1, 1.5

[56] References Cited

U.S. PATENT DOCUMENTS 3,965,254 0/1976 Tofe et al.
4,361,544 11/1982 Goldenberg ..................... 424/1

OTHER PUBLICATIONS

Zamenhof, et al., "Boron Neutron Capture Therapy for the Treatment of Cerebral Gliomas. I: Theoretical Evaluation of the Efficacy of Various Neutron Beams*", Medical Physics 2 (1975), 47–59.
Escher, et al., "L-Carboranylalanine Substituted TMV, a Highly Boron Labelled Virus as a Model for Slow Neutron Therapy of Tumors", J. Labelled Comp. Radiopharm., vol. XIV (1978), 487–496.
Wong, et al., "Boron Hydride Derivatives for Neutron Capture Therapy Antibody Approach", J. Med. Chem. 17 (1974), 785–791.
Sneath, et al., "Protein–Binding Polyhedral Broanes. 1", J. Med Chem. 17 (1974), 796–799.
Zakharkin, et al., "Synthesis of o–Carboranyl–Substituted Phosphonous Acids", Izv. Akad. Nauk. SSSR, 9 (1969), 2056–2057.
Zakharkin, et al., "Synthesis of o–Carboranylphosphonic Acids", Zh. Obsch. Khim., 41 (1971), 588–592.

Primary Examiner—Christine M. Nucker
Attorney, Agent, or Firm—Jacobus C. Rasser; Steven J. Goldstein; Jack D. Schaeffer

[57] ABSTRACT

Boron containing polyphosphonates of the formula

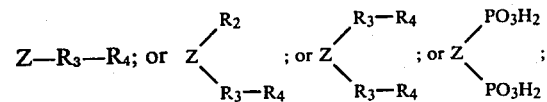

wherein Z is a boron-containing radical; $R_2$ is an alkyl group containing from 1 to about 10 carbon atoms; $R_3$ is a geminal diphosphonate or a vicinal polyphosphonate containing up to 10 phosphonic acid radicals; $R_4$ is hydrogen, lower alkyl, amino, benzyl, halogen, hydroxyl, —$CH_2COOH$, —$CH_2PO_3H_2$, or —$CH_2CH_2PO_3H_2$; and the salts and esters thereof, have high affinity for calcified tissues, in particular calcific tumors. The compounds are useful in boron neutron capture therapy of such tumors.

34 Claims, No Drawings

BORON CONTAINING POLYPHOSPHONATES FOR THE TREATMENT OF CALCIFIC TUMORS

TECHNICAL FIELD

This invention relates to novel compounds suitable for boron neutron capture therapy for the treatment of calcific tumors; i.e. primary and metastatic bone tumors and soft tissue calcifying tumors. The novel compounds of this invention are boron containing polyphosphonates.

The technique of boron neutron capture therapy (BNCT) for the treatment of tumors involves the selective loading of the tumor with a $^{10}B$ containing boron compound and subsequent irradiation with thermal or epithermal neutrons. The neutron capture reaction, $^{10}B(n, alpha)^7Li$, releases an alpha particle and a recoiling $^7Li$ ion with an average total kinetic energy of 2.33 MeV. These charged particles have a range in tissue of less than 10 microns which is comparable to or less than a cell diameter. Consequently, the radiation does distribution due to these particles follows the boron distribution in the irradiated tissue even to the cellular level. BNCT, therefore, combines the attractive features of both external beam and internal radioisotope therapy to deliver a large differential dose to the boron loaded tumor cells dispersed within healthy tissue.

For successful application of this therapy a high tissue specificity of the boron containing compound is of vital importance. Boron compounds synthesized thus far lack this required tissue specificity. For example, in the boron neutron capture treatment of brain tumors, a small amount of the boron compound gets adsorbed on the walls of capillaries and small arterials within the normal brain, resulting in radiation damage to vital healthy tissues.

A different approach, applicable solely to the treatment of calcified tumors, has been the use of di- or polyphosphonates containing $^{32}P$ or $^{33}P$. Due to the high affinity to calcified tissues, these radioactive phosphonates are adsorbed on calcific tumors. The beta radiation from the radioactive phosphorus isotope destroys malignant tumor cells. An important disadvantage of this method of therapy is that the radioactivty is present in the compounds when they are traveling in the bloodstream to the tumor site. As a result the whole body is exposed to radiation in this method of therapy. Moreover, the range of beta particles in tissues is much longer than that of alpha particles or ions of similar energy. The range of beta particles eminating from radioactive phosphorus isotopes is several cell diameters and damage to bone marrow is an important and highly undesirable side effect of this method of therapy.

Prior to the present invention no compounds or methods existed, whereby short range radiation could be generated within the tumor tissue without a substantial risk of radiation damage to healthy tissue.

Accordingly, it is the object of this invention to provide a means for introducing quantities of $^{10}B$ isotope in calcified tumors which upon irradiation with thermal or epithermal neutrons generate short range particles destroying the tumor cells without simultaneously damaging non-tumorous bone, bone marrow and soft tissue cells. It has now been discovered that the above object can be achieved by using the novel boron containing phosphonates of this invention. Compositions comprising these compounds can be administered orally or intravenously. Upon irradiation with collimated low energy neutrons the boron generates short range radiation which destroys the malignant cells.

BACKGROUND ART

Application of boron neutron capture therapy in the treatment of cerebral gliomas is discussed by Zamenhof, et al., Medical Physics 2 (1975) 47–59. Discussing the failure of earlier experiments, the authors point out that optimization of the neutron source will increase the chances of therapeutic success somewhat. However, success mainly depends on the availability of $^{10}B$ compounds which exhibit a high $^{10}B$ tumor-to-blood partition rather than those which achieve high absolute levels of $^{10}B$ in the tumor.

Escher, et al., J. Labelled Comp. Radiopharm., Vol. XIV (1978) 487–96, report on a newly synthesized carborane-containing amino acid, which can be easily tagged to a protein. A model test with tobacco mosaic virus was not successful, because of the high number of receptor sites in the protein. Other boron-containing compounds capable of interaction with proteins are disclosed by Wong, et al., J. Med. Chem. 17 (1974) 785–91, and by Sneath, et al., J. Med. Chem. 17 (1974) 796–9.

The use of $^{32}P$ and $^{33}P$ containing phosphonates in the treatment of calcific tumors is disclosed in U.S. Pat. No. 3,965,254, granted June 22, 1976 to Tofe and Francis.

Zakharkin, et al., Izn. Akad. Nauk. SSSR, 9 (1969) 2056-7, disclose the synthesis of several o-carboranyl phosphines and of methyl-o-carboranylphosphorus acid. Zakharkin, et al., Zh. Obsch. Khim., 41 (1971) 588-92, disclose the preparation of (methyl-o-carboranyl) phosphonic acid, (phenyl-o-carboranyl) phosphonic acid, and o-carboranyl phosphonic acid. The synthesis of o-carboranyl diphosphonates is not disclosed.

DETAILED DESCRIPTION OF THE INVENTION

By "polyphosphonate" herein is meant a compound containing two or more phosphonic acid ($-PO_3H_2$) groups, and esters and salts thereof.

By "diphosphonate" herein is meant a compound containing two phosphonic acid groups, and esters and salts thereof.

By "o-carborane" herein is meant 1,2-dicarba-closododeca borane (12), denoted by

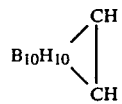

The compounds of this invention are boron containing polyphosphonates of the formula

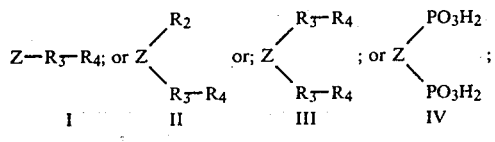

wherein Z is a boron-containing radical; $R_2$ is an alkyl group containing from 1 to about 10 carbon atoms; $R_3$ is

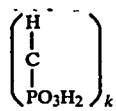

wherein k is an integer of from 2 to 10, or

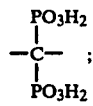

$R_4$ is hydrogen, lower alkyl, amino, benzyl, halogen, hydroxyl, —CH$_2$COOH, —CH$_2$PO$_3$H$_2$, —CH$_2$CH$_2$PO$_3$H$_2$; and the salts and esters thereof.

More particularly, the compounds of this invention include boron-containing polyphosphonates of the formula

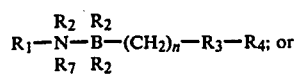   V

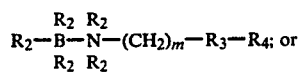   VI

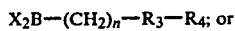   VII

VIII

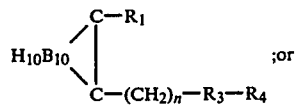

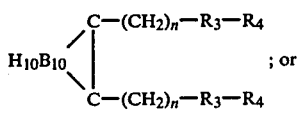   IX

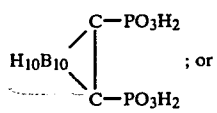   X

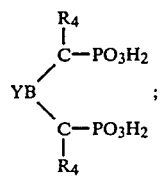   XI

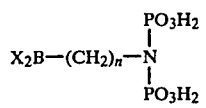   XII wherein X is benzyl, phenyl, naphthyl, lower alkyl, halogen, alkoxy, diol, or hydroxyl; Y is benzyl, phenyl, halogen, hydroxyl, naphthyl or amine; $R_1$ is hydrogen or an alkyl group containing from 1 to 24 carbon atoms; $R_2$ is hydrogen or an alkyl group containing from 1 to 10 carbon atoms; n is an integer from 0 to 10; m is an integer from 1 to 10; $R_3$ is

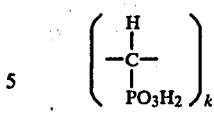

wherein k is an integer of from 2 to 10, or

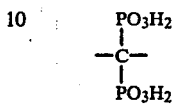

or an ester or a salt thereof; $R_4$ is halogen, hydrogen, OH, NH$_2$ or CH$_2$OH.

Operable boron containing polyphosphonates of the above formula I include dibromo (propyl-1,2,3-triphosphonic acid) methylborane; (butyl-1,2.3.4-tetraphosphonic acid) methyl boronic acid; ethyl-2-(pentyl-1,2,3,4,5-pentaphosphonic acid) dichloro borane; 2-(hexyl-1,2,3,4,5,6-hexaphosphonic acid) ethyl boronic acid; methyl-(heptyl-1,2,3,4,5,6,7-hepta phosphonic acid) amino methyl borane, (propyl-2,2-diphosphonic acid) dimethyl borane dichloro, 1-(2-amino, 2-methyl, 3-hydroxy 3,3 propanediphosphonic acid) propyl borane; dimethyl, 3-(2-(1-hydroxy 1,1-diphosphonomethyl) pyrolidinyl borane; and salts and esters thereof, e.g. sodium, potassium, calcium, magnesium, ammonium, triethanolammonium, diethanol ammonium, and monoethanolammonium salts, and e.g. methyl, ethyl, i-propyl, propyl, butyl and t-butyl esters of the above acids.

Among the operable boron-containing polyphosphonates of the above formulae II and III are 1-methyl, 2-(2,2-ethane diphosphonic acid) dicarbaclosotriborane (5); 1-ethyl, 5(1,2,3-propane triphosphonic acid) dicarbaclosotriborane (5); 1,6-di(1,2,3,4-butane tetraphosphonic acid) dicarbaclosotetraborane (6); 1,2-di(ethane-2-carboxy-1,1-diphosphonic acid) dicarbaclosononaborane (12); 1-methyl, 6-(2-chloro, 2,2-ethane diphosphonic acid)-dicarbaclosooctacarborane (8); 1-ethyl, 7-(2-hydroxy, 2,2-ethane diphosphonic acid)-dicarbaclosododecarborane (12); 1,12-di(5-fluoro, 5-5 pentane diphosphonic acid) dicarbaclosododecarborane (12); and 1-propyl, 2-(pent-4-ene-1-hydroxy-1,1-diphosphonic acid) dicarbaclosododecarborane (12); and salts, e.g. sodium, potassium, calcium, magnesium, ammonium, triethanol ammonium, diethanolammonium, and monoethanolammonium salts of the above acids; and esters, e.g. methyl, ethyl, i-propyl, propyl, butyl and t-butyl esters of the above acids.

Among the operable boron-containing polyphosphonates of the above formula IV are diphosphono-o-carborane; dimethyl, 1-(3-N,N-diphosphonoamine)-propyl borane; dichloro, (N,N-diphosphonoamine) methyl borane; methyl diphosphonoborane; isopropyldiphosphonoborane; t-butyldiphosphonoborane; 1-methyl, 2-(4-N,N-di(methylphosphonoamino)butyl)-o-carborane; and salts, e.g. sodium, potassium, calcium, magnesium, ammonium, triethanolammonium, diethanolammonium and monoethanolammonium salts of the above acids; and esters, e.g. methyl, ethyl, isopropyl, propyl and t-butyl esters of the above acids.

The compounds of this invention are characterized in that they contain at least one boron atom, and at least two geminal or at least two vicinal phosphonic acid radicals, provided that when the compound contains two vicinal phosphonic acid radicals said radicals must be in cis position, which means that the compound must be e.g. cyclic or an olefin to allow for such a position. Compounds of this genus possess a high affinity for aclcified tissues in humans and lower animals. In addition to this general calcific activity, these compounds exhibit a specific selectivity for calcific tumors, so that effective amounts of $^{10}B$ an be delivered to such tumors without adversely affecting non-tumorous sites.

The affinity for calcified tissues of the compounds of this invention resides in the polyphosphonate moiety of these compounds. This affinity of polyphosphonates is well known, as evidenced by e.g. U.S. Pat. No. 3,683,080, granted Aug. 8, 1972 to Francis. It has now surprisingly been found that when a boron containing moiety is attached to such polyphosphonates, the high affinity for calcified tissues is retained. In other words, the presence of one or more boron-carbon bonds, in spite of the highly polar character of such bonds, appears not to affect significantly the calcium affinity of the polyphosphonates. Importantly, the compounds of this invention also share a high specific selectivity for calcified tumors.

The boron isotope useful in the neutron capture treatment of tumor tissues is $^{10}B$, which has a natural abundance of about 20%. Due to the high affinity for calcified tumors possessed by the compounds of the present invention it is possible to deposit effective amounts of $^{10}B$ in these tissues when the natural isotope mixture of boron is used. The effectiveness can of course be increased by using isotope mixtures which are "enriched" in $^{10}B$, i.e. contain significantly more than 20% $^{10}B$.

Any boron containing polyphosphonate is suitable for the deposition of $^{10}B$ in calcified tumor tissue. The boron containing moiety Z in formulas I through IV may be a boron hydride radical, e.g. beryl, 1-diboran (6) yl, tetraboran (10) yl; or the radical of a boron hydride derivative, e.g. chloroiodoboranyl, 1-methyldiboran (6) yl, hydroxyphenylboranyl, butylethoxyboranyl, B-dimethylmethylaminoboranyl; or a boron containing ring structure, e.g. the radicals of 1,3,2-diazaborol, 1,3,2-dioxaborolane, 1,5-diboracyclooctane; or the radical of boronic or borinic acid, e.g. 2-aminoethyl ester of diphenylborinic acid, benzene boronic acid, butyldiethoxyborane, bis(dimethylamino)-methylborine; or carboranes, e.g. dicarbaclosopentaborane (5), monocarbanido hexaborane, 1,7-dicarbaclosoheptaborane (9), 1,2-dicarbaclosodecarborane (12). The compounds of the formulas V through XII are most conveniently synthesized, and are preferred herein. The polyphosphonate moiety is preferably a geminal diphosphonate i.e. a diphosphonic acid of the formula

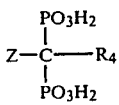

and salts and esters thereof.

Carboranes contain more than one boron atom and are therefore the preferred boron-containing moieties. More preferred are the dicarbadecaboranes, as they contain a desirably high number of boron atoms; all three isomers of dicarbadecarborane (12) are equally suitable for use herein, o-carborane can be conveniently synthesized and is therefore most preferred for use herein.

A polyphosphonate containing polymethylene group may be attached to only one of the carbon atoms of the carborane cage, in which case the other carbon atom is preferably substituted with an alkyl group (formula VIII). The preferred alkyl group in compounds of this type is methyl. As mentioned before, the preferred polyphosphonate is a geminal diphosphonate. The hydrogen atom on the terminal carbon atom may be substituted with an OH group, an amino group or a Cl atom, e.g. 1-methyl, 2-(2-chloro, 2-2-ethanediphosphonic acid-o-carborane; 1-methyl, 2-(2-hydroxy, 2-2-ethanediphosphonic acid)-o-carborane.

In another embodiment of this invention both carborane carbon atoms are substituted with a polymethylene polyphosphonate (formula IX). As before, the preferred polyphosphonate of the genus of formula IX is the geminal diphosphonate. The hydrogen atom on the terminal carbon atoms may be substituted with an OH group, an amino group of a Cl atom, e.g. 1,2-di(2-chloro 2,2-ethanediphosphonic acid)-o-carborane; 1,2-di(2-hydroxy-2,2-ethane diphosphonic acid)-o-carborane.

In still anothr embodiment of this invention, the phosphonate groups are attached directly to the carbon atoms of the carborane cage (formula X).

SYNTHESIS

The synthesis of the polyphosphonates is disclosed in U.S. Pat. No. 3,683,080, granted Aug. 8, 1972 to Francis, and references cited herein. The disclosures thereof are incorporated herein by reference.

The preparation of organic compounds of boron is disclosed in Hagihara, et al., "Handbook of Organometallic Compounds", Ch. 3, Published by W. A. Benjamin, Inc., New York 1968, and references cited therein. The disclosures thereof are incorporated herein by reference.

The synthesis of carboranes and substituted carboranes is disclosed in Grimes, "Carboranes", Published by Academic Press, New York 1970, and references cited herein. The disclosures thereof are incorporated herein by reference.

The coupling of a polyphosphonate to an organic boron compound can be done by standard organic synthesis techniques, and will be apparent to the skilled organic synthetic chemist. The process of making these novel compounds is therefore not part of this invention. However, a number of alternative synthesis routes are given below.

(a) Carbanion attack of a halogenated borane, e.g.

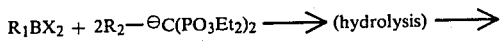

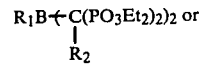

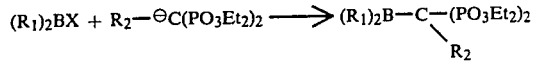

(b) Hydroboration of an alkene polyphosphonate with catechol borane, e.g.

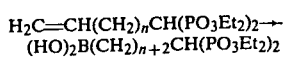

(c) Reaction of a boron containing carboxylic acid with $PCl_3$ and $H_3PO_3$, e.g.:

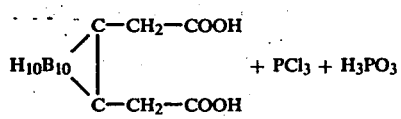

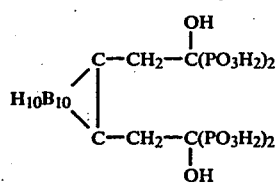

(d) Reaction of a boron containing nitrile with PBr$_3$, e.g.:

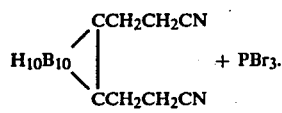

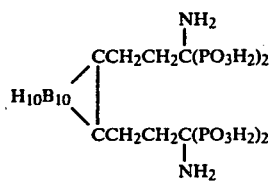

(e) Reaction of a boron hydride with a polyphosphonate containing an amino group, e.g.

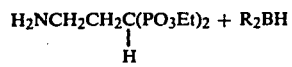

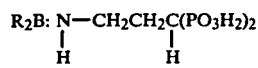

(f) Direct attachment of the phosphonic acid radicals to the boron atom, e.g.

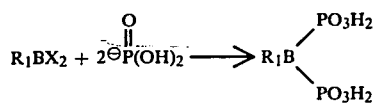

(g) Reaction with a diazonium compound, e.g.

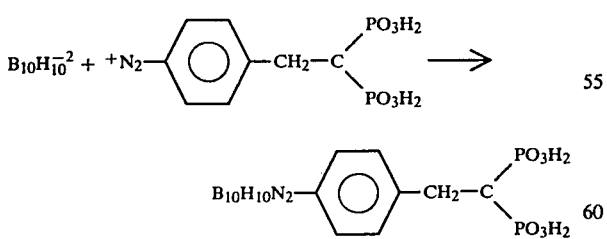

The principle of this synthesis is disclosed by Hawthorne, et al., J. Am. Chem. Soc. 87 (1965) 2366–72, disclosure of which is incorporated herein by reference.

Several representative syntheses using a carbanion intermediate are disclosed in full detail in the following examples.

EXAMPLE I

Synthesis of 1-methyl, 2-(tetra ethyl 2,2-ethane diphosphonate)-o-carborane.

Step 1 Preparation of tetrasodium vinyl diphosphonate (Na$_4$VDP)

103 g Tetrasodium 1-hydroxyethane-1,1-diphosphonate (Na$_4$EHDP) was put into a 500 ml round bottom flask and heated in a fluidized sand bath at 400° C.±25° C. for 70 minutes. The reaction flask was being rotated and was under aspiration pressure of about 20 mm Hg (about 2.6×10$^3$ N/m$^2$). Vigorous evolution of gas was obvious during heating. The reaction product was cooled to room temperature and mixed with 210 ml H$_2$O and about 2 g charcoal. The solution was boiled for about 15 minutes and filtered through paper under vacuum. The product was precipitated from the solution by freeze/thaw initiated crystallization, and purified by repeated recrystallization. The purified crystals were filtered off and dried at about 110° C. for 4 hrs.

Step 2 Ion exchange to H$_4$VDP

Tetrasodium vinyl diphosphonate was converted to the acid form as follows:

A solution of 18 g Na$_4$VDP in water was run down an ion exchange resin column (AG 50 N- X 8) in the acid form. The eluent was collected (about 300 ml) and evaporated on a rotovac. The viscous oil was put on a lyophilizer overnight.

Step 3 Preparation of tetraethyl vinyl diphosphonate

The vinyl diphosphonic acid was removed from the lyophilizer; 100 ml (EtO)$_3$CH was added thereto, and the mixture was heated in an oil bath. Evolving EtOH and EtOC(O)H were distilled off.

The reaction product was vacuum distilled at about 300 micron mercury (about 40 N/m$^2$) pressure. The fraction boiling at 132°–135° C. was collected, and identified by $^{31}$P NMR as tetraethyl vinyl diphosphonate; yield 8.5 g.

Step 4 Preparation of 1-methyl, 2-(tetra-ethyl-2,2-ethane diphosphonate)-o-carborane.

To a 100 ml round bottom flask were added 2.0 g 1-methyl-o-carborane (Dexsil) and 50 ml dry THF; 10 ml of a 1.6 M solution of n-butyllithium were added dropwise at 5° C. The mixture was kept at 5° C., and 3.5 g tetraethyl vinyldiphosphonate was added dropwise. Subsequently, the reaction mix was stirred in ice for 30 minutes, then allowed to warm to room temperature and stirred for another 60 minutes. The solution obtained was red in color. After addition of 10 ml distilled water the color turned yellow.

The THF was evaporated, and the reaction mixture extracted twice with 25 ml diethyl ether. The ether fractions were combined, dried with magnesium sulfate and filtered through paper. On evaporation of the ether, 5.9 g of a yellow oil was obtained. $^{31}$P NMR showed a single peak at 22.1 ppm.

In like manner, the following compounds are prepared:

1-methyl, 2-(tetramethyl-2,2-ethane diphosphonate)-o-carborane; 1-ethyl, 2-(tetraethyl-2,2-ethane diphosphonate)-o-carborane; 1-propyl, 2-(tetraethyl-2,2-ethanediphosphonate)-o-carborane; 1-ethyl, 7-tetraethyl-2,2-ethane diphosphonate)-dicarbaclosododecarborane (12); 1-butyl, 2-(tetraethyl-2,2- ethane diphosphonate)-dicarbacloso-triborane (5);
1-pentyl, 6-(tetraethyl-2,2-ethane diphosphonate)-dicarbaclosooctacarborane (8); and 1-butyl, 12-(tetraethyl-2,2-ethane diphosphonate)dicarbaclosododecarborane (12).

EXAMPLE II

Preparation of 1-methyl, 2-(tetraethyl 2-chloro, 2,2-ethane-diphosphonate)-o-carborane.

To 1.0 g 1-methyl, 2-(tetraethyl 2,2-ethane-diphosphonate)-o-carborane (Example I) was added 50 ml Clorox[R]. The mixture was stirred for 60 hrs in ice, then extracted with two times 25 ml diethyl ether. The ether fractions were combined, dried with magnesium sulfate and filtered through paper. The ether was evaporated on rotovac. The resulting oil was identified as the monochloro tetraethyl ester by $^1$H NMR, $^{31}$P NMR and $^{11}$B NMR.

In the same manner, 2-methyl, 3-(tetraethyl 2-chloro-2,2-ethane diphosphonate)-tetranidocarborane (8); 1-ethyl, 2-(tetrapropyl 2-chloro-2,2-ethane diphosphonate)-trinidocarborane (7); and 1-isopropyl, 6-(tetramethyl 2-chloro-2,2-ethane diphosphonate)-dicarbaclosotetracarborane (6) are prepared from the corresponding esters.

EXAMPLE III

Preparation of 1-methyl, 2-(2,2-ethane diphosphonic acid)-o- carborane.

To 5.9 g 1-methyl, 2-(tetra ethyl 2,2-ethane diphosphonate)-o-carborane (Example I) was added 50 ml 6 N HCl. The solution was refluxed overnight. A white solid precipitated. The HCl solution was evaporated on rotovac. The structure of the 1-methyl, 2-(2,2-ethane diphosphonic acid)-o-carborane thus obtained was verified with $^{31}$P, $^{13}$C, $^1$H and $^{11}$B NMR. In the same manner, 1-methyl, 2-(tetraethyl 2-chloro-2,2-ethane diphosphonate)-o-carborane was converted to 1-methyl, 2-(2-chloro-2,2-ethane diphosphonic acid)-o-carborane.

The sodium salts were obtained by dissolving the acids in a solution of sodium hydroxide.

In the same manner, the other esters of Examples 1 and 2 are converted to the corresponding acids and their salts.

EXAMPLE IV

Synthesis of 1,2-di-(tetraethyl 2,2-ethane diphosphonate)-o-carborane. 1.50 g o-Carborane (10.4 mmole) was dissolved in 30 ml dry THF under nitrogen and cooled to about 5° C.; 14 ml n-butyllithium (21 mmole) was added dropwise under stirring. After about half of the butyllithium was added a white precipitate was formed.

6.90 g Vinyl diphosphonate (ethyl ester) (23 mmole) was mixed with about 7 ml dry THF and added to the carborane carbanion solution under stirring at 5° C. The white precipitate dissolved after about half of the disphosphonate was added. After completion of the vinyl diphosphonate addition the reaction mixture was allowed to warm up to room temperature. The solution was yellow in color; 10 ml water was added to it, and the mixture was stirred at room temperature for about one hour. The two phases were separated, and the water phase washed twice with diethyl ether. The ether phase and the THF phase were combined and the solvent was evaporated. The resulting oil was confirmed to be 1,2-di-(tetraethyl 2,2-ethane-diphosphonate)-o-carborane by $^{31}$P NMR. Part of the ester was hydrolized to 1,2-di-(2,2-ethane diphosphonic acid)-o-carborane, using the method of Example III. Another part of the ester was monochlorinated to 1,2-di-(tetraethyl 2-chloro-2,2-ethane diphosphonate)-o-carborane, according to the method of Example II, and subsequently hydrolyzed to 1,2-di(2-chloro-2,2-ethane diphosphonic acid)-o-carborane.

In the same manner the following compounds are prepared:

1,5-di(tetramethyl-2,2-ethane diphosphonate)-dicarbaclosotriborane (5); 1,2-di(tetramethyl-2,2-ethane diphosphonate)-dicarbaclosotriborane (5); 1,6-di(tetraisopropyl 2,2-ethane diphosphonate)-dicarbaclosotetraborane (6); 1,2-di(tetrabutyl 2,2-ethane diphosphonate)-dicarbaclosotetraborane (6); 2,4-di(tetraisobutyl 2,2-ethane diphosphonate)-dicarbaclospentaborane (7); 1,7-di(tetra-t-butyl 2,2-ethane diphosphonate)-dicarbaclosohexaborane (8); 1,6-di(tetrapentyl 2,2-ethane diphosphonate)-dicarbaclosooctaborane (10); 1,10-di(tetrahexyl 2,2-ethane diphosphonate)-dicarbaclosooctaborane (10); 1,7-di(tetramethyl 2,2-ethane diphosphonate)-dicarbaclosododecarborane (12); and 1,12-di(tetraethyl 2,2-ethane diphosphonate)-dicarbaclosododecarborane (12); and the corresponding monochlorinated esters, acids, monochlorinated acids, salts and monochlorinated salts.

EXAMPLE V

Synthesis of 1,2-diphoshono-o-carborane.

1,2-Diphosphono-o-carborane was prepared as follows: To a solution of 5 g o-carborane in dry THF was added dropwise 46.7 ml of a 1.5 N solution of n-butyllithium at 0° C. To the mixture was then quickly added 11 g diethyl chlorophosphite. The solution was refluxed for several hours. The THF was evaporated. The resulting residue contained unreacted o-carborane and 1,2-di(diethyl phosphite) o-carborane. The latter was hydrolized to the corresponding acid in 500 ml 6 N HCl by refluxing during 24 hours, after which the remaining HCl solution was evaporated. The residue was dissolved in 500 ml water; unreacted o-carborane, which is not soluble in water, was filtered off. The water was then evaporated, and the residue mixed with 50 ml 10% hydrogen peroxide. The mixture was carefully refluxed until the reaction was completed. The structure of 1,2-diphosphono-o-carborane was verified by $^{31}$P and $^{11}$B NMR.

In substantially the same manner the following compounds are prepared:

1,5-diphosphonodicarbaclosotriborane (5);
1,2-diphosphonodicarbaclosotriborane (5);
1,6-diphosphonodicarbaclosotetraborane (6);
1,2-diphosphonodicarbaclosotetraborane (6);
2,4-diphosphonodicarbaclosopentaborane (7);
1,7-diphosphonodicarbaclosohexaborane (8);
1,6-diphosphonodicarbaclosooctaborane (10);
1,10-diphosphonodicarbaclosooctaborane (10);
1,7-disphosphonodicarbaclosododecarborane (12); and
1,12-diphosphonodicarbaclosododecarborane (12).

EXAMPLE VI

Synthesis of difluoro, (methane diphosphonic acid) borane. Difluoro, (methane diphosphonic acid)-borane was prepared as follows: To a 100 ml 3 necked round bottom flask were added 30 ml dry THF and 2.3 g (1.0 mmole) tetraethyl methane diphosphonate; 0.70 ml of a 1.6 N solution of butyllithium (1,1 mmole) were added slowly at 0° C. The solution was drawn up in a 50 ml syringe and added slowly to 1.42 g BF$_3$.OEt$_2$ (1 mmole) in 30 ml dry THF at 0° C. under stirring. The product was hydrolyzed to difluoro, (methanediphosphonic acid)-borane. Upon further hydrolysis dihydroxy, (methane-diphosphonic acid)-borane is formed.

In a similar fashion are synthesized dimethyl (methane diphosphonic acid)borane; benzyl, chloro (3,3-propane diphosphonic acid)borane; dimethyl (2,2-ethane diphosphonic acid)borane; difluoro (1,2,3-propane triphosphonic acid)borane; diphenyl (1,2,3,4-butane tetraphosphonic acid)borane; phenyl chloro (1,2,3,4,5-pentane pentaphosphonic acid)borane; diisopropyl (1,2,3,4,5,6-hexane hexaphosphonic acid)borane; dichloro (1,2,3,4,5,6,7-heptane hepta phosphonic acid)borane; dibromo (1,2,3,4,5,6,7,8-octane octaphosphonic acid)borane; dihydroxy(1,2,3,4,5,6,7,8,9-nonanenonaphosphonic acid)borane; ethyl, methyl (1,2,3,4,5,6,7,8,9,10-decanedecaphosphonic acid)borane; dinaphthyl (2-hydroxy-2,2-ethane diphosphonic acid)borane; ditoluyl (1-nonane 9,9-diphosphonic acid)borane; difluoro (1-carboxy-2,2-ethane diphosphonic acid)borane; dichloro (2-chloro-2,2-ethane diphosphonic acid)borane; dibromo(2-hydroxy-2,2-ethane diphosphonic acid,)borane; diiodo (2-amino-2,2-ethane diphosphonic acid)borane; and dimethyl (N,N-dimethyl amino methane diphosphonic acid)borane.

EXAMPLE VII

To 10 mmole of tetraethyl methylene diphosphonate in dry THF is added dropwise 7 ml of a 1.5 N solution of n-butyllithium at 0° C. The mixture is stirred for about a half hour. About 5 mmole 1,2-di(2-chloroethane)-o-carborane is mixed with 3 ml dry THF and added to the diphosphonate carbanion solution under stirring at 5° C. After completion of the carborane addition the solution is allowed to warm up to room temperature. 5 ml water are added and the mixture is stirred at room temperature for about one hour. The THF phase is then separated, and the solvent evaporated in a rotovac. The remaining oil is 1,2-di(tetraethyl 3,3-propane diphosphonate)-o-carborane. Part of the product is chlorinated to 1,2-di(tetraethyl 3-chloro-3,3-propane diphosphonate)-o-carborane.

In the same manner the following additional compounds are prepared:

1,2-di(tetramethyl 4,4-butane diphosphonate)-o-carborane; 1,2-di(tetrapropyl 5,5-pentane diphosphonate)-o-carborane; 1,7-di(tetrabutyl 6,6-hexanediphosphonate)-dicarbaclosododecarborane (12); 1,12-di(tetraisopropyl 7,7-heptane diphosphonate)-dicarbaclosododecarborane (12); and 1,12-di(tetraisopropyl 7 chloro-7,7-heptane-diphosphonate)-dicarbaclosododecarborane (12).

In one of its aspects, this invention is a composition in unit dosage form comprising from about 0.5 mg to about 1000 mg, preferably from about 15 mg to about 1000 mg, of a boron-containing polyphosphonate of the formula I, II, III, or IV or a pharmaceutically acceptable salt or ester thereof, and a pharmaceutical carrier. Preferred for use in these compositions are the compounds of the formulas V through XI. The polyphosphonate moiety preferably is a geminal diphosphonate. For reasons discussed hereinbefore, o-carborane diphosphonates are highly preferred. Most preferred are the hydroxyl substituted o-carborane diphosphonates.

The required dosage of boron containing polyphosphonates will vary with the size of the tumor being treated, the degree of calcification of this tumor, the boron compound being used, the $^{10}$B content of that compound, and like factors. Once deposited in the tumor, the boron compound will remain there. It is therefore possible to load the tumor tissue with $^{10}$B by frequently administering small quantities of the compound in the course of a number of days. Many of the boron compounds of this invention are lipophilic and will initially be taken up by the liver and only slowly released to the bloodstream. The optimum daily dosage will depend largely on the general condition of the patient and will have to be determined by the attending physician on a case by case basis. Generally, single dosages can range from 0.01 to 500 mg per kg of body weight, preferably from 0.5 to 50 mg/kg (unless otherwise specified, the unit designated "mg/kg" as used herein refers to mg boron compound per kg of body weight) with up to four dosages daily. Dosages greater than about 500 mg/kg may produce toxic symptoms and are to be avoided. Dosages of less than about 0.01 mg/kg do not result in a significant deposition of $^{10}$B at the tumor site, even administered intravenously.

For purposes of oral administration the boron polyphosphonates can be formulated in the form of capsules, tablets or granules.

The preferred concentration range of boron polyphosphonate in unit dosage from is from 15 mg to 1000 mg, more preferably 100 mg to 500 mg.

As used herein, the term "pharmaceutical carrier" denotes a solid or liquid filler diluent or encapsulating substance. Some examples of the substances which can serve as pharmaceutical carriers are sugars such as lactose, glucose and sucrose; starches such as corn starch and potato starch; cellulose and its derivatives, such as sodium carboxymethylcellulose, ethylcellulose, cellulose acetate; powdered tragacanth; malt; gelatin, talc; stearic acid; magnesium stearate; calcium sulfate; vegetable oils, such as peanut oil, cottonseed oil, sesame oil, oilve oil, corn oil and oil of theobroma; polyols such as propylene glycol, glycerin, sorbitol, mannitol, and polyethylene glycol; agar; alginic acid; pyrogen-free water; isotonic saline; and phosphate buffer solutions, as well as other non-toxic compatible substances used in pharmaceutical formulations. Wetting agents and lubricants such as sodium lauryl sulfate, as well as coloring agents, flavoring agents and perservatives, can also be present.

The pharmaceutical carrier employed in conjunction with the polyphosphonates is used at a concentration sufficient to provide a practical size to dosage relationship. Preferably, the pharmaceutical carrier comprises from about 0.1 percent to 99 percent by weight of the total composition.

After a sufficient amount of $^{10}$B has been deposited in the tumor tissue, the tumor site is irradiated with thermal or epithermal neutrons. Preferably, an epithermal neutron beam with a mean energy of 37 eV is used in the boron neutron capture therapy. A suitable neutron source is D$_2$O moderated and $^{10}$B-filtered $^{252}$Cf. The method of generating neutron beams suitable for use in boron neutron capture therapy is disclosed by Zamenhof, et al., Med. Phys. 2 (1975) 47-60, incorporated herein by reference.

A neutron source of $^{252}$Cf in D$_2$O yields about $2.6 \times 10^{12}$ n.s$^{-1}$. The beam is filtered with $^{10}$B and focused with a lithium loaded collimator. After collimation the flux is about $2.4 \times 10^8$ neutrons cm$^{-2}$ s$^{-1}$. The particles have a relaxation length of approximately 2.7 cm in soft tissue. The tumor site is irradiated with a radiation dose of about 200 rad.

Crystal Growth Inhibition Test

The potential affinity of the boron polyphosphonates for calcified tissues is demonstrated by the Crystal Growth Inhibition Test. This test was developed for the non-boron containing polyphosphonates to establish their potential to reduce calcium phosphate deposition, and has been shown to be predictive of the affinity of these compounds for calcified tissues like bone (see U.S. Pat. No. 3,683,080, granted Aug. 8, 1972 to Francis) and for calcified tumor tissue (see U.S. Pat. No. 3,965,254, granted June 22, 1976 to Tofe et al.). The test is conducted as follows:

50 ml of a 0.01 M $KH_2PO_4$ stock solution is diluted with 1000 ml $N_2$ purged distilled water. 1 ml of an aqueous solution of the polyphosphonate to be tested (at a concentration to provide the desired ultimate concentration in the reaction mixture) is added to the diluted $KH_2PO_4$ solution and the solution is adjusted to pH 7.4 with potassium hydroxide. To this solution is added 50 ml of a 0.0175 N $CaCl_2$ solution preadjusted to pH 7.4. The KOH consumption is recorded as a function of time. The rate of KOH consumption is directly related to the rate of calcium phosphate formation. In the absence of polyphosphonate the formation of calcium phosphate starts at t=o, i.e. when the solutions of $KH_2PO_4$ and $CaCl_2$ are mixed. Low levels of polyphosphonates are capable of inhibiting the formation of calcium phosphate for 20 minutes or longer. This effect depends on the propensity of the polyphosphonates to adsorb on calcium phosphate crystal nuclei.

1-Methyl, 2-(2,2-ethane diphosphonic acid) o-carborane (MECB) was subjected to the Crystal Growth Inhibition Test. Ethane hydroxy diphosphonate (EHDP) and dichloromethylene diphosphonate ($Cl_2MDP$), compounds which have a high affinity for calcified tumor tissue, were subjected to the same test.

Table I below shows that the capability of MECB to retard the formation of calcium phosphate is the same as that of $Cl_2MDP$, indicating that the two compounds have similar affinity to calcified tumor tissue.

TABLE I

| Compound | Concentration Mole | Lag Time Minutes |
| --- | --- | --- |
| $Cl_2MDP$ | $1 \times 10^{-6}$ | 18 |
| EHDP | $1 \times 10^{-6}$ | 82 |
| MECB | $1 \times 10^{-6}$ | 25 |
| $Cl_2MDP$ | $2 \times 10^{-6}$ | 41 |
| MECB | $2 \times 10^{-6}$ | 37 |

ANIMAL SKELETAL UPTAKE TEST

In this test the skeletal uptake of a polyphosphonate compound is established as follows:

A reducing solution is prepared by mixing 5.0 ml of a 0.34 N NTA solution, 1.0 ml of a 0.84 M $SnCl_2$ solution and 3.0 ml $H_2O$. The pH of the solution is adjusted to 5.6 with 1.0 N NaOH. 100 ul of the reducing solution is added to 1.0 ml of a $^{99m}TcO_4^-$ solution, containing 19.6 mCi. The reduction of $TcO_4^-$ is checked by TLC. 0.9 ml of a 35 mg/ml solution of a boron polyphosphonate is added to the reduced technetiate solution. Rabbits are injected with 1.0 ml each of this solution. The animals are scanned for skeletal uptake at 3 hrs and 21 hrs after injection.

When subjected to the above described test, MECB showed high skeletal affinity.

EXAMPLE VIII

Capsules are prepared by conventional methods, comprised as follows:

| Ingredient | mg per Capsule |
| --- | --- |
| MECB* | 350.00 |
| Starch | 55.60 |
| Sodium lauryl sulfate | 2.90 |

*1-methyl, 2-(2,2 ethane diphosphonic acid)-o-carborane, prepared as in example III To a 76 kg adult with a bone tumor are administered orally twice daily the above capsules for a period of ten days. About 24 hrs after the last capsule is administered, the tumor site is irradiated with a 37 eV neutron beam of $2.4 \times 10^8$ neutrons $cm^{-2}s^{-1}$. An effective level of alpha and Li particles is generated in the tumor tissue.

Similar results are attained when 1,2-di-(2,2-ethane diphosphonic acid)-o-carborane, 1,2-diphosphono-o-carborane, 1-methyl, 2-(2-chloro-2,2-ethane diphosphonic acid)-o-carborane, 1-ethyl, 2(2-hydroxy-2,2-ethane sodium diphosphonate)-o-carborane, dimethyl (methane diphosphonic acid) borane, phenyl (2,2-ethane ammonium diphosphonate) borane, and dihydroxy tetraethyl-4,4 butane diphosphonate) borane, respectively, are employed in the above described capsule in place of MECB.

EXAMPLE IX

Tablets are prepared by conventional methods, formulated as follows:

| Ingredient | mg per tablet |
| --- | --- |
| DClEDP* | 25.00 |
| Lactose | 40.00 |
| Starch | 2.50 |
| Magnesium Stearate | 1.00 |

*1,2-di(2-chloro-2,2-ethane diphosphonic acid)-o-carborane prepared as in Examples II and III.

When administered orally four times daily, the above composition deposits significant amounts of $^{10}B$ in the calcified tumor tissue of a patient with such tumor. Upon irradiation of the tumor site by 37 eV, neutrons effective levels of localized alpha particles are emitted.

Similar results are obtained with tablets formulated as above but replacing DClEDP with 1,7-di(3-amino-3,3 propane-diphosphonic acid) dicarbaclovododecarborane (12), dibutyl (N-amino-3,3-propanediphosphonic acid) borane, fenyl diphosphonoborane, dihydroxy (tetramethyl 3-hydoxy-3,3-propane diphosphonate) borane and dichloro (1,2,3 propane triphosphonic acid) borane, respectively.

Solutions for parental administration are prepared by dissolving the following boron diphosphonates in distilled water at the specified concentration, adjusting the pH to 7.4 with the base corresponding to the indicated salt form, or sodium hydroxide in the case of the acids, and sterilizing same by standard sterilization techniques.

| Example | Boron Polyphosphonate | Conc., mg/ml |
|---|---|---|
| X | 1,7-di(1,2,3,4 butane tetraphosphonic acid) dicarbaclosohepta borane (9) | 10.0 |
| XI | 1,2-di(diethyl phosphonate)-o-carborane | 15.0 |
| XII | 1-propyl, 2-(5,5 pentane-sodium diphosphonate)-o-carborane | 25.0 |
| XIII | difluoro (6,6-hexanediphosphonic acid) borane | 5.0 |
| XIV | dimethyl (dimethyl methanediphosphonate) borane | 23.0 |

The solutions of the foregoing examples when administered by injection to animals afflicted with bone tumors deposit significant amounts of $^{10}B$ in the bone tumor tissues.

I claim:

1. Boron containing polyphosphonates selected from the group consisting of: Z—R$_3$—R$_4$;

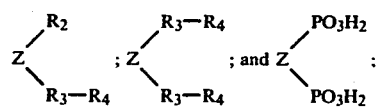

wherein Z is a boron-containing radical; R$_2$ is an alkyl group containing from 1 to about 10 carbon atoms; R$_3$ is

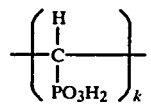

wherein k is an integer of from 2 to 10, or

R$_4$ is hydrogen, lower alkyl, amino, benzyl, halogen, hydroxyl, —CH$_2$COOH, —CH$_2$PO$_3$H$_2$, or —CH$_2$CH$_2$PO$_3$H$_2$; and the salts and esters thereof.

2. Boron containing polyphosphonates selected from the group consisting of those having the formula:

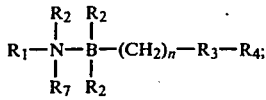

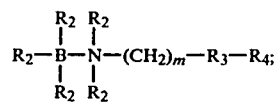

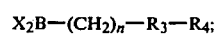

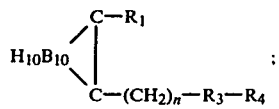

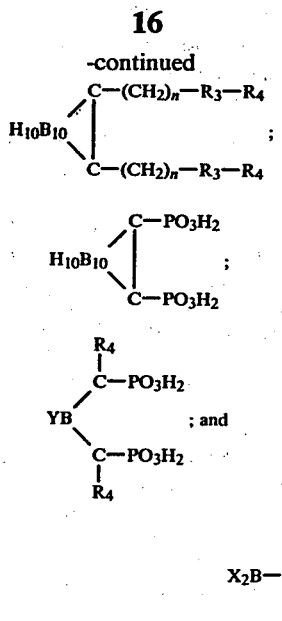

$$X_2B-(CH_2)_n-\underset{\underset{PO_3H_2}{|}}{\overset{\overset{PO_3H_2}{|}}{N}}$$

wherein X is benzyl, phenyl, naphthyl, lower alkyl, halogen alkoxy, diol, or hydroxyl; Y is benzyl, phenyl halogen, hydroxyl naphthyl or amine; R$_1$ is hydrogen or an alkyl group containing from 1 to 24 carbon atoms; R$_2$ is hydrogen or an alkyl group containing of from 1 to 10 carbon atoms; n is an integer from 0 to 10; m is an integer from 1 to 10; R$_3$ is

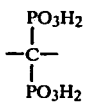

wherein k is an integer of from 2 to 10, or

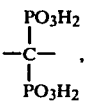

or an ester or a salt thereof; R$_4$ is halogen, hydrogen, OH, NH$_2$ or CH$_2$OH.

3. The polyphosphonates of claim 1 wherein R$_3$ is $$-\underset{\underset{PO_3H_2}{|}}{\overset{\overset{PO_3H_2}{|}}{C}}-,$$

and salts and esters thereof.

4. Boron containing diphosphonates of the formula

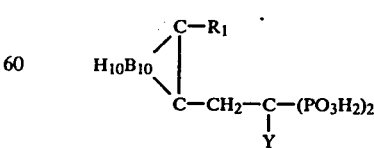

wherein R$_1$ is hydrogen or an alkyl group containing from 1 to 10 carbon atoms; Y is H, OH, NH$_2$ or Cl, and esters and salts thereof.

5. Boron containing diphosphonates of the formula

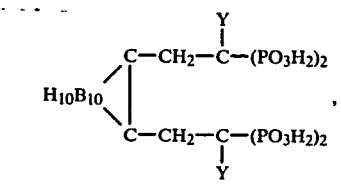

wherein Y is H, OH, $NH_2$ or Cl; and esters and salts thereof.

6. The disphosphonates of claim 3 wherein $R_1$ is methyl.

7. The compound of the formula

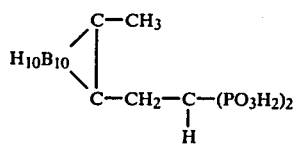

and esters and salts thereof.

8. The compound of the formula

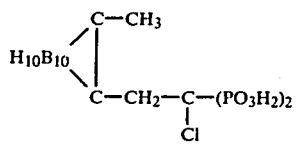

and esters and salts thereof.

9. The compound of the formula

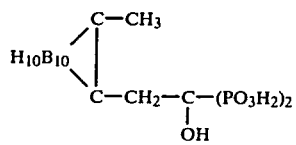

and esters and salts thereof.

10. The compound of the formula

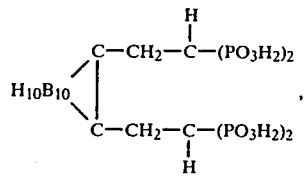

and esters and salts thereof.

11. The compound of the formula

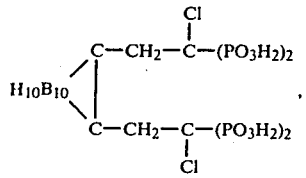

and esters and salts thereof.

12. The compound of the formula

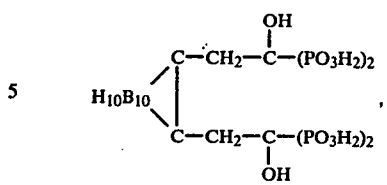

and esters and salts thereof.

13. The compound of the formula

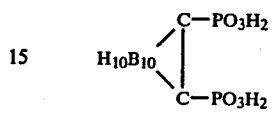

and esters and salts thereof.

14. A composition in unit dosage form comprising (1) from about 15 mg to about 1000 mg of a boron containing polyphosphonate selected from the group consisting of:

$$Z-R_3-R_4;$$

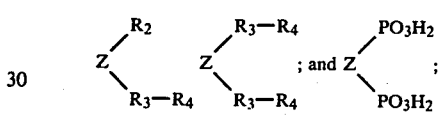

wherein Z is a boron-containing radical; $R_2$ is an alkyl group containing from 1 to about 10 carbon atoms; $R_3$ is

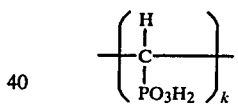

wherein k is an integer of from 2 to 10, or

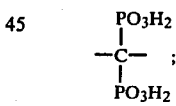

$R_4$ is hydrogen, lower alkyl, amino, benzyl, halogen, hydroxyl, $-CH_2COOH$, $-CH_2PO_3H_2$, or $-CH_2CH_2PO_3H_2$; and the pharmaceutically acceptable salts and esters thereof, and (2) a pharmaceutical carrier.

15. A composition in unit dosage form comprising (1) from about 15 mg to about 1000 mg of a compound selected from the group of boron containing compounds of the formula:

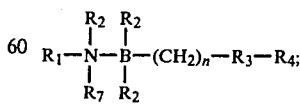

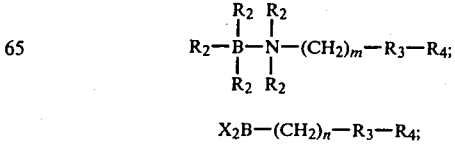

$$X_2B-(CH_2)_n-R_3-R_4;$$

-continued

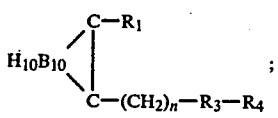

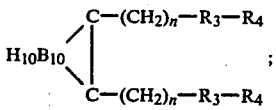

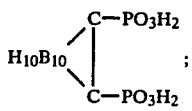

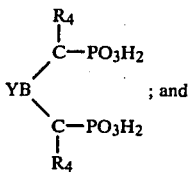

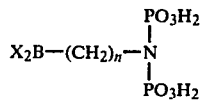

wherein X is benzyl, phenyl, naphthyl, lower alkyl, halogen alkoxy, diol, or hydroxyl; Y is benzyl, phenyl halogen, hydroxyl naphthyl or amine; $R_1$ is hydrogen or an alkyl group containing from 1 to 24 carbon atoms; $R_2$ is hydrogen or an alkyl group containing of from 1 to 10 carbon atoms; n is an integer from 0 to 10; m is an integer from 1 to 10; $R_3$ is

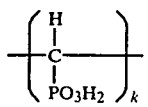

wherein k is an integer of from 2 to 10, or

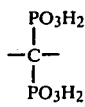

or an ester or a salt thereof; $R_4$ is halogen, hydrogen, OH, $NH_2$ or $CH_2OH$, and (2) a pharmaceutical carrier.

16. The composition of claim 15 wherein $R_3$ is

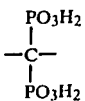

and the pharmaceutically acceptable salts and esters thereof.

17. A composition in unit dosage form comprising (1) from about 15 mg to about 1000 mg of a compound selected from the group of carborane diphosphonates of the formula

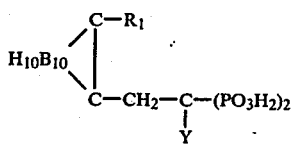

wherein Y is H, OH, $NH_2$ or Cl, and the pharmaceutically acceptable salts and esters thereof, and (2) a pharmaceutical carrier.

18. A composition in unit dosage form comprising (1) from about 15 mg to about 1000 mg of a compound selected from the group of carborane diphosphonates of the formula

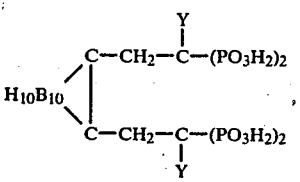

wherein Y is H, OH, $NH_2$ or Cl, and the pharmaceutically acceptable salts and esters thereof, and (2) a pharmaceutical carrier.

19. The composition of claim 17 wherein $R_1$ is methyl.

20. The composition of claim 17 wherein the carborane diphosphonate is 1-methyl, 2-(2,2 ethanediphosphonic acid)-o carborane, or a salt or ester thereof.

21. The composition of claim 17 wherein the carborane diphosphonate is 1-methyl, 2-(2-chloro, 2-2 ethanediphosphonic acid)-o-carborane, or a salt or ester thereof.

22. The composition of claim 18 wherein the carborane diphosphonate is 1,2-di(2,2-ethanediphosphonic acid)-o-carborane, or a salt or ester thereof.

23. The composition of claim 18 wherein the carborane diphosphonate is 1,2-di(2-chloro-2,2 ethanediphosphonic acid)-o-carborane, or a salt or ester thereof.

24. A composition in unit dosage form comprising (1) from about 15 mg to about 1000 mg 1,2-diphosphono-o-carborane, or a salt or ester thereof, and (2) a pharmaceutical carrier.

25. A method for the treatment of calcific tumors comprising administering to an animal afflicted therewith a safe but effective dose of a compound selected from the group of boron containing polyphosphonates of the formula $Z-R_3-R_4$;

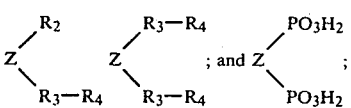

wherein Z is a boron-containing radical; $R_2$ is an alkyl group containing from 1 to about 10 carbon atoms; $R_3$ is

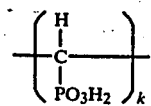

wherein k is an integer of from 2 to 10, or

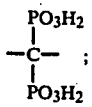

R$_4$ is hydrogen, lower alkyl, amino, benzyl, halogen, hydroxyl, —CH$_2$COOH, —CH$_2$PO$_3$H$_2$, or —CH$_2$CH$_2$PO$_3$H$_2$; and the salts and esters thereof and the pharmaceutically acceptable salts and esters thereof; and subsequent irradiation of the tumor site with thermal or epithermal neutrons.

26. A method for the treatment of calcific tumors comprising systemically administering to an animal afflicted therewith a safe but effective dose of a compound selected from the group of boron containing polyphosphonates of the formula:

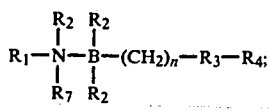

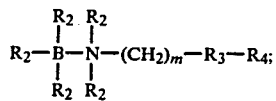

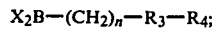

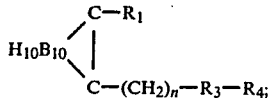

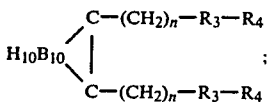

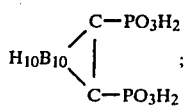

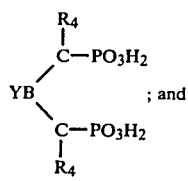

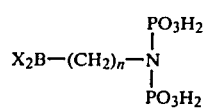

wherein X is benzyl, phenyl, naphthyl, lower alkyl, halogen alkoxy, diol, or hydroxyl; Y is benzyl, phenyl halogen, hydroxyl naphthyl or amine; R$_1$ is hydrogen or an alkyl group containing from 1 to 24 carbon atoms; R$_2$ is hydrogen or an alkyl group containing of from 1 to 10 carbon atoms; n is an integer from 0 to 10; m is an integer from 1 to 10; R$_3$ is

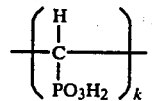

wherein k is an integer of from 2 to 10, or

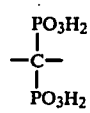

or an ester or a salt thereof; R$_4$ is halogen, hydrogen, OH, NH$_2$ or CH$_2$OH and the pharmaceutically acceptable salts and esters thereof; and subsequent irradiation of the tumor site with thermal or epithermal neutrons.

27. The method of claim 25 wherein R$_3$ is

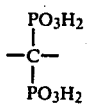

or an ester or a salt thereof.

28. The method of claim 26 wherein the boron containing polyphosphonate has the formula

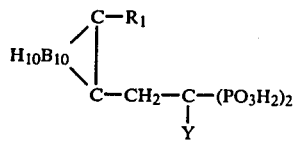

wherein Y is H, OH, NH$_2$ or Cl, and esters and salts thereof.

29. The method of claim 26 wherein the boron containing polyphosphonate has the formula

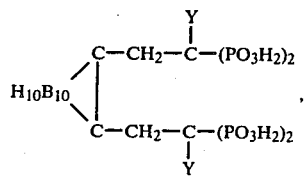

wherein Y is H, OH, NH$_2$, or Cl, and esters and salts thereof.

30. The method of claim 26 wherein the boron containing polyphosphonate is 1-methyl, 2-(2,2 ethanediphosphonic acid)-o-carborane, or a pharmaceutically acceptable salt or ester thereof.

31. The method of claim 26 wherein the boron containing polyphosphonate is 1-methyl, 2-(2-chloro, 2-2 ethanediphosphonic acid)-o-carborane, or a pharmaceutically acceptable salt or ester thereof.

32. The method of claim 26 wherein the boron containing polyphosphonate is 1,2-di(2,2-ethanediphosphonic acid)-o-carborane, or a pharmaceutically acceptable salt or ester thereof.

33. The method of claim 26 wherein the boron containing polyphosphonate is 1,2-di(2-chloro-2,2-ethanediphosphonic acid)-o-carborane, or a pharmaceutically acceptable salt or ester thereof.

34. The method of claim 26 wherein the boron containing polyphosphonate is 1,2-diphosphono-o-carborane or a pharmaceutically acceptable salt or ester thereof.

* * * * *